(12) United States Patent
Lea (10) Patent No.: US 6,403,384 B1
(45) Date of Patent: Jun. 11, 2002

(54) DEVICE AND METHOD FOR ANALYZING A BIOLOGIC SAMPLE

(75) Inventor: Peter Lea, Toronto (CA)

(73) Assignee: Umedik, Inc., Toronto (CA)

( * ) Notice: Subject to any disclaimer, the term of this patent is extended or adjusted under 35 U.S.C. 154(b) by 0 days.

(21) Appl. No.: 09/335,732

(22) Filed: Jun. 18, 1999

(30) Foreign Application Priority Data

Nov. 16, 1998 (CA) .............................................. 2254223

(51) Int. Cl.[7] ...................... G01N 33/543; G01N 21/00; C12M 3/00; B01D 15/00; B01D 24/00
(52) U.S. Cl. ........................ 436/518; 436/523; 436/805; 436/809; 435/287.2; 435/287.3; 435/288.6; 422/59; 422/60; 422/63; 422/70; 422/72; 210/198.1; 210/198.2; 210/263; 210/268
(58) Field of Search .................... 210/198.1, 198.2, 210/263, 268; 422/59, 60, 63, 70, 72; 435/287.2, 287.3, 288.6; 436/523, 518, 805, 809

(56) References Cited

U.S. PATENT DOCUMENTS

| | | | | |
|---|---|---|---|---|
| 3,492,396 A | * | 1/1970 | Dalton et al. .................. | 424/12 |
| 3,905,767 A | | 9/1975 | Morris et al. .................. | 23/230 |
| 4,088,448 A | | 5/1978 | Lilja et al. ..................... | 23/259 |
| 4,381,921 A | | 5/1983 | Pierce et al. .................. | 436/535 |
| 4,425,438 A | * | 1/1984 | Bauman et al. ............... | 436/527 |
| 4,430,436 A | | 2/1984 | Koyama et al. ............... | 436/531 |
| 4,447,546 A | | 5/1984 | Hirschfield ................... | 436/527 |
| 4,452,759 A | | 6/1984 | Takekawa ..................... | 422/73 |
| 4,477,575 A | | 10/1984 | Vogel et al. .................. | 436/170 |
| 4,521,522 A | | 6/1985 | Lundstrom et al. .......... | 436/525 |
| 4,690,907 A | * | 9/1987 | Hibino et al. ................. | 436/514 |
| 4,753,776 A | | 6/1988 | Hillman et al. ............... | 422/101 |
| 4,790,640 A | * | 12/1988 | Nason .......................... | 350/534 |

(List continued on next page.)

FOREIGN PATENT DOCUMENTS

| | | |
|---|---|---|
| JP | 07068785 | 3/1995 |
| WO | WO 96/14933 | 5/1996 |
| WO | WO 96/19739 | * 6/1996 |

OTHER PUBLICATIONS

Suketu et al. Effect of viscosity and interfacial tension on particle size of cellulose acetate trimellitate microspheres. J. Microencapsulation. (1992) vol. 9, No. 2, pp. 215–227.*
Joanne Stephensen, RAMP: A quantitative immunoassay platform takes shape, IVD Technology, Jul./Aug. 1998, pp. 51–56.
Basic Principles of Immunoassay and Other Binding Assays, pp. 185, 186, 205, 619.
ROC Analysis.
Kamalakar Gulukota, Skipping a step with neural nets, Nature Biotechnology, vol. 16, Aug. 1998, pp. 722 and 723.
Letters, Clinical Chemistry 44, No. 4, 1998 pp. 890–891.
Johan Ellenius, et al., Early assessment of patients with suspected acute myocardial infarction by biochemical monitoring and neural network analysis, Clinical Chemistry 43:10, pp. 1919–1925, 1997.
Theresa Weicker, Receiver Operating Characteristics Analysis, School of Health Information Science, Faculty of Human and Social Development, University of Victoria, 1997.
"What is an Artificial Neural Network?", Battelle Memorial Institute, 1997.

*Primary Examiner*—Christopher L. Chin
*Assistant Examiner*—Kartic Padmanabhan
(74) *Attorney, Agent, or Firm*—Lyon & Lyon LLP (57) ABSTRACT

A device and method for separating a fluid component from a non-fluid component of a sample comprises a plurality of microspheres disposed in abutting relation and forming therebetween a plurality of capillary channels, whereby when the microspheres are disposed in fluid communication with a sample the fluid component is separated from the non-fluid component by capillary flow of the fluid component through the capillary channels formed by the interstitial spacing between abutting microspheres.

25 Claims, 3 Drawing Sheets

U.S. PATENT DOCUMENTS

| | | | | |
|---|---|---|---|---|
| 4,839,297 A | | 6/1989 | Freitag et al. | 436/170 |
| 4,846,182 A | | 7/1989 | Fogt et al. | 128/632 |
| 4,943,522 A | | 7/1990 | Eisinger et al. | 435/7 |
| 4,990,259 A | * | 2/1991 | Kearney et al. | 210/659 |
| 5,039,617 A | | 8/1991 | McDonald et al. | 436/69 |
| 5,073,484 A | | 12/1991 | Swanson et al. | 435/7.92 |
| 5,077,012 A | | 12/1991 | Giurguis | 422/58 |
| 5,110,724 A | | 5/1992 | Hewett | 435/11 |
| 5,118,428 A | | 6/1992 | Sand et al. | 210/749 |
| 5,132,097 A | | 7/1992 | Van Deusen et al. | 422/82 |
| 5,135,719 A | | 8/1992 | Hillman et al. | 422/101 |
| 5,219,763 A | * | 6/1993 | Van Hoegaerden | 436/523 |
| 5,278,205 A | * | 1/1994 | Siddiqui et al. | 523/219 |
| 5,300,779 A | | 4/1994 | Hillman et al. | 250/341 |
| 5,338,689 A | * | 8/1994 | Yves et al. | 436/518 |
| 5,384,264 A | | 1/1995 | Chen et al. | 436/525 |
| 5,415,841 A | * | 5/1995 | Dovichi et al. | 422/68.1 |
| 5,458,852 A | | 10/1995 | Buechler | 422/58 |
| 5,504,013 A | | 4/1996 | Senior | 436/165 |
| 5,514,537 A | * | 5/1996 | Chandler | 435/2 |
| 5,536,470 A | | 7/1996 | Frey et al. | 422/56 |
| 5,540,888 A | | 7/1996 | Bunce et al. | 422/100 |
| 5,569,364 A | * | 10/1996 | Hooper et al. | 204/455 |
| 5,580,794 A | | 12/1996 | Allen | 436/169 |
| 5,589,401 A | * | 12/1996 | Hansen et al. | 436/525 |
| 5,610,077 A | | 3/1997 | Davis et al. | 436/518 |
| 5,653,884 A | * | 8/1997 | Smart et al. | 210/634 |
| 5,679,526 A | | 10/1997 | Buechler et al. | 435/7.1 |
| 5,716,778 A | * | 2/1998 | Weng et al. | 435/4 |
| 5,725,768 A | * | 3/1998 | Adachi et al. | 210/435 |
| 5,738,992 A | | 4/1998 | Cook et al. | 435/6 |
| 5,753,517 A | | 5/1998 | Brooks et al. | 436/514 |
| 5,763,360 A | * | 6/1998 | Gundel et al. | 502/402 |
| 5,766,961 A | | 6/1998 | Pawlak et al. | 436/510 |
| 5,770,460 A | | 6/1998 | Pawlak et al. | 436/510 |
| 5,814,524 A | * | 9/1998 | Walt et al. | 436/518 |
| 5,821,066 A | | 10/1998 | Pyle et al. | 435/7.2 |
| 5,837,546 A | | 11/1998 | Allen et al. | 436/169 |
| 5,855,782 A | * | 1/1999 | Falkenhagen et al. | 210/323.1 |
| 5,866,345 A | * | 2/1999 | Wilding et al. | 435/7.21 |
| 5,869,345 A | | 2/1999 | Chandler | 436/514 |
| 5,879,881 A | * | 3/1999 | Rubenstein | 435/5 |
| 5,912,116 A | | 6/1999 | Caldwell et al. | 435/5 |
| 6,010,463 A | | 1/2000 | Lauks et al. | 600/576 |
| 6,046,058 A | | 4/2000 | Sun | 436/514 |
| 6,066,258 A | * | 5/2000 | Gjerde et al. | 210/635 |
| 6,103,537 A | * | 8/2000 | Ullman et al. | 436/526 |

* cited by examiner

DEVICE AND METHOD FOR ANALYZING A BIOLOGIC SAMPLE

FIELD OF THE INVENTION

This invention relates to a device for separating a fluid component, such as plasma, from a biologic sample, such as blood, using microspheres and analyte specific labeling. This invention also relates to a device and method for quantitative determination of an amount of analyte present in biologic fluids. The invention further relates to a quantitative. assay method and device for measuring one or more analytes in a biologic fluid sample using a point-of-care assay method and device. The test results can be analyzed using a suitable analyzer and, optionally, the assay test results are transmitted by way of digital transmission systems to permit further evaluation of the data.

BACKGROUND OF THE INVENTION

There are presently many examples of one step assays for measuring analytes in fluid. A common assay is the pregnancy test device which involves contacting a urine sample with a test pad, which urine moves by capillary flow along the bibulous chromatography strips whereby the presence of human chorionic gonadotropin (HCG) will be detected usually as shown by a coloured line because of the reaction between HCG and reagents in the bibulous chromatography strips. This is an example of a chromatographic assay.

U.S. Pat. No. 5,766,961 issued Jun. 16, 1998 and U.S. Pat. No. 5,770,460 issued Jun. 23, 1998 are both entitled "One-Step Lateral Flow Nonbibulous Assay". "Nonbibulous lateral flow" refers to liquid flow in which all of the dissolved or dispersed components of a liquid, which are not permanently entrapped or filtered out, are carried at substantially equal rates and with relatively unimpaired flow laterally through a stabilized membrane. This is distinguished from preferential retention of one or more components as would occur, for example, in materials capable of absorbing or imbibing one or more components, as occurs in chromatographic configurations. In this one-step assay, a sample (which may contain the analyte of interest) is collected on the "sample receiving zone" from which it flows to the "labelling zone" at which point it encounters a specific binding reagent for the analyte coupled to visible moieties (the "assay label"), then flows to a "capture zone" where the analyte bound to visible moieties is captured.

In U.S. Pat. No. 5,540,888 issued Jul. 30, 1996 and entitled "Liquid Transfer Assay Devices", the invention described is a device for biochemical diagnostic assays. It comprises two liquid flow channels of porous material which transfer liquid by capillary flow to a common site following simultaneous application of the liquid to the ends of the channels. The channels interconnect at a certain point and then both continue in an arrangement analogous to an electrical bridge circuit. By selecting the hydraulic resistances of the arms of this circuit, the flow can be controlled across the bridge.

U.S. Pat. No. 5,300,779 issued Apr. 5, 1994 entitled "Capillary Flow Device" describes methods and devices for measuring an analyte in a sample mixed with reagents, the devices defining a flow path. The specific binding by agglutination may provide for changes in flow rate, light patterns of a flowing medium, or light absorption or scattering which permit measurement of the analyte of interest.

In U.S. Pat. No. 5,110,724 issued May 5, 1992, entitled "Multi-Analyte Device", the invention described is an assay device for assaying multiple analytes in a drop-sized blood sample. A dispenser distributes a small volume blood sample to multiple transfer sites by capillary flow of the blood sample through sieving and distributing matrices which separate blood cells from plasma as the sample fluid migrates toward the transfer sites. A test plate in the device carries multiple absorbent pads, each containing reagent components for use in detection of a selected analyte. The test plate is mounted on the dispenser toward and away from a transfer position at which the exposed surface regions of the pads are in contact with associated sample-transfer sites, for simultaneous transfer of sample fluid from such sites to the pads in the support.

In U.S. Pat. No. 5,039,617 entitled "Capillary Flow Device and Method for Measuring Activated Partial Thromboplastin Time", the invention described measures "activated partial thromboplastin time" (APTT) on a whole blood sample by applying the sample to a capillary tract with reagents capable of initiating an APTT analysis, wherein clotting time is measured by the cessation of blood flow in the capillary tract. This is an example of a risk evaluation based on coagulation.

In U.S. Pat. No. 4,753,776 entitled "Blood Separation Device Comprising a Filter and a Capillary Flow Pathway Exiting the Filter", the invention describes a method for separating plasma from red blood cells. The driving force for the movement of plasma from the filter to the reaction area of a device utilizing the method is capillary force provided by a tubular capillary. A filter is selected from glass microfiber filters of specified characteristics.

The U.S. Pat. No. 5,135,719 issued Aug. 4, 1992, entitled "Blood Separation Device Comprising a Filter and Capillary Flow Pathway Exiting the Filter", the similar invention is described and the glass fibre filters are prepared from fibers with diameters between 0.10 and 7.0 µm.

In U.S. Pat. No. 4,447,546 issued May 8, 1984, entitled "Fluorescent Immunoassay Employing Optical Fibre in Capillary Tube", a short length of precise diameter capillary tubing with an axially disposed optical fibre to which is immobilized a monolayer of a component of the antibody antigen complex (eg. an antibody) is described. The tubing is immersed in the sample.

U.S. Pat. No. 5,610,077 issued Mar. 11, 1997, entitled "Processes and Apparatus for Carrying Out Specific Binding Assays", describes the well known antibody binding to antigen assay. The sample which may contain the analyte (a), (the substance being tested for) is mixed with (b) an antibody which binds to the substance being tested for, which antibody is immobilized on a solid support, and (c) another antibody for the substance being tested for which is conjugated to a detectable marker, to thereby form a complex between (b), the substance being tested for and (c) and causes the marker to be immobilized and detected.

In U.S. Pat. No. 4,943,522 issued Jul. 24, 1990, entitled "Lateral Flow, Non-Bibulous Membrane Assay Protocols", the described invention is a method and apparatus for conducting specific binding pair assays, such as immunoassays, the test substrate is a porous membrane on which a member of the binding pair is affixed in an "indicator zone". The sample is applied and is permitted to flow laterally through the indicator zone and any analyte in the sample is complexed with the affixed specific binding member, and detected. A novel method of detection employs entrapment of observable particle in the complex, for instance, red blood cells of blood can be used as the observable particles for detection of the complex.

An example of a method to separate red blood cells from whole blood samples is found in U.S. Pat. No. 5,118,428 issued Jun. 2, 1992, entitled "Method to Remove Red Blood Cells from Whole Blood Samples". In the described invention, red blood cells are removed from whole blood samples with a solution containing an acid. The agglutinated red blood cells are then removed from the resulting suspension by procedures of filtration, centrifugation or decantation, leaving an essentially red blood cell-free serum or plasma sample.

In U.S. Pat. No. 5,073,484, entitled "Quantitative Analysis Apparatus and Method", an analyte is measured along a liquid flow path which includes a number of reaction-containing reaction zones spaced apart along the flow path. Detector means are employed to detect analyte, reactant or predetermined product in the reaction zones, the number of zones in which detection occurs indicating the amount of analyte in the liquid.

In U.S. Pat. No. 5,536,470 issued Jul. 16, 1986, entitled "Test Carrier for Determining an Analyte in Whole Blood", red blood cells cannot gain access from the blood sample application side, to the detection side and on the detection side as a result of an analysis reaction, an optically detectable change occurs.

A serious deficiency in current one-step assays for the measurement and/or detection of an analyte is that they provide only qualitative results rather than quantitative results. That is to say that the presence or absence of the analyte may be determined but the actual amount or concentration of analyte present in the sample would still not be known. The assay of the present invention provides quantitative results as the test is performed in a determinable volume. In the prior art methods it is not possible to consistently identify the exact volume of the test sample in repeated testings since the fluids must wash through the test strips.

Prior art methods using chromatographic strips and fiberglass strips require larger initial volumes of the biologic fluid in order to mobilize the proteins and labels in the strips. This is particularly true when the biologic fluid is blood and the plasma must first be separated from the blood sample. An advantage of the device and method of the present application is that very small fluid samples can be used to measure one or more analytes. The assay method and device of the present invention is also advantageous because the test volume can be made constant and therefore repeated testings will yield quantitative data which can be directly compared between samples and within a sample.

It is an advantage of the present invention that the assay device and methodology allows for separation of the plasma from the whole blood during the assaying of a fluid sample. In other words it is not necessary to previously separate out the cellular component of the blood before assaying the sample. This is a significant advantage as it allows that the assay can be used at the point of patient care, for example, by the patient themself, at the patient's bedside or in a doctor's office. In a preferred embodiment of the present invention there is provided by the device and assay methodology of the present invention a generic point-of-care platform suitable for use in one or more diagnostic or prognostic assays performed on one or more fluid samples.

SUMMARY OF THE INVENTION

In accordance with an aspect of the present invention a method for separating out the fluid component of a biologic sample using microspheres is provided. In one embodiment, the biologic sample is placed in contact with a group of microspheres and the fluid component separates from the sample as the fluid portion flows through the microspheres, by capillary action.

In accordance with an aspect of the present invention a quantitative assay method and device are provided for measuring one or more analytes in a fluid sample using a point-of-care assay method and device. The assay and device are designed for use by a patient themself, at the bedside of a patient, or in a doctor's office. The test results are analyzed using a suitable analyzer and, optionally, the assay test results are transmitted by way of digital transmission systems to permit further evaluation of the data by an off-site professional.

In accordance with an aspect of the present invention, an assay method and portable assay device are provided for testing small volumes of biologic fluids, including blood, in a timely manner. In accordance with another aspect of the present invention, a method and device are provided for testing samples of biologic fluids in which a consistent volume of the biologic fluid sample is tested for one or more analytes and the data generated from the tests are used for collecting and compiling in a database pertaining, for example, to a particular disease condition. Ultimately the data collected can be used to train neural network algorithms and the algorithms may then be used to provide diagnostic and/or prognostic information based on the individual test results of any given test subject.

In accordance with another aspect of the present invention in respect to the analysis of blood, the cellular components of blood are separated from plasma by allowing the whole blood to be exposed to microsphere beads which permit the plasma to pass in the spaces formed between the microspheres by capillary action but not the cellular component. The present invention is not limited to the separation of cells from plasma in blood but includes broader applications where microsphere beads may be used to separate a fluid component from a cellular component in a biologic fluid. The microsphere beads are effectively acting as a fluid filter.

According to another aspect of the present invention a device is provided for separating plasma from blood in a sample. The device comprises a plurality of microspheres disposed in abutting relation and forming therebetween a plurality of capillary channels, whereby when the microspheres are disposed in fluid communication with a blood sample cellular and plasma components of the biologic sample are separated by capillary flow of the plasma component through the capillary channels formed by the interstitial spacing between abutting microspheres.

According to another aspect of the present invention the device comprises a plurality of groups of smaller microspheres each impregnated with a different label and interspersed with the larger microspheres in separate zones of the larger microspheres. The microspheres may be of substantially the same diameter, or the microspheres may be of differing diameters. The size of microsphere selected may be based on the viscosity of the sample or the size of the component one wishes to exclude or separate.

In accordance with yet another aspect of the present invention, the microspheres are bundled in a fluid-permeable material or the microspheres are maintained in abutting relation by a surface tension of the fluid which passes through them, for example plasma. In accordance with yet another aspect of the present invention the microsphere beads, also known simply as microspheres, are dried on a surface of the device.

In accordance with another aspect of the present invention, the device comprises a sample shelf adjacent to the fluid entrance and the microspheres are disposed on the sample shelf.

According to yet another aspect of the present invention the device comprises a plurality of smaller microspheres which are impregnated with at least one label interspersed with a plurality of larger microspheres such that the smaller microspheres occupy the interstitial spacing between the larger microspheres and release a label into the fluid as it flows through the interstitial spacing between the larger microspheres. There may be a plurality of groups of smaller microspheres each impregnated with a different label and interspersed with the larger microspheres in separate zones of the larger microspheres. Alternatively, the smaller microspheres may be mobilized and carried forward by the fluid as it passes along the capillary channels formed by the larger microspheres.

In accordance with another aspect of the present invention, the device comprises an indicator containing patient identification information to be associated with results of the assay, for example a bar code which can be read by a bar code reader.

According to another aspect of the present invention, a method of separating fluid from a biologic sample is provided. The sample has a fluid component and a non-fluid component and the method comprises the steps of, (a) bringing the sample into fluid communication with a plurality of microspheres disposed in abutting relation and forming therebetween a plurality interstitial spaces which connect to comprise capillary channels, and (b) collecting the fluid component as it is separated by capillary flow of the fluid component through the capillary channels. According to another aspect of the present invention there is provided, a method of conducting an assay utilizing a device comprising a capillary chamber defined by first and second opposed surfaces spaced a capillary distance apart having a fluid entrance and at least one reagent disposed within the capillary chamber, comprising the steps of, (a) conveying a fluid sample into fluid communication with the fluid entrance such that the fluid sample is drawn into the capillary chamber by capillary action and reacts with the reagent, and (b) analyzing the reagent to determine whether the reagent binds to an analyte in the fluid sample.

According to another aspect of the present invention the method further comprise the step of analyzing the reagent to determine a proportion of the reagent which binds to the sample.

According to another aspect of the present invention, the method further comprises a plurality of capillary chambers for conducting a plurality of assays on one or more fluid samples. According to another aspect of the present invention the results of the tests are recorded in a computer database and may be further applied in a trained neural network algorithm to generate a profile of one or more selected disorders. The assay further comprising the step of applying a receiver operating characteristic analysis to the data to determine a statistical significance of the data.

In accordance with another aspect of the present invention a wick or a capillary is brought into fluid communication with the fluid sample to remove the fluid sample from the capillary chamber.

In accordance with another aspect of the present invention microspheres are used to separate a cellular component from a fluid component in a biologic fluid, for example plasma from whole blood, and the fluid component can be tested in chromatography test strips. Furthermore, the microsphere beads of the present invention may be used as a labeling device, in addition to a filtration device, in standard nitrocellulose chromatography assays.

Other and further details of this preferred embodiments are described in the Detailed Description of the Preferred Embodiments together with the drawings described below.

BRIEF DESCRIPTION OF THE DRAWINGS

For the purpose of illustrating the invention, there is shown in the drawings a form which is presently preferred. It is not intended that this invention be limited to the precise arrangements and instrumentalities shown. The present invention will be described in detail with reference to the accompanying drawings, in which like numerals denote like parts in the several views, and in which.

DETAILED DESCRIPTION OF THE PREFERRED EMBODIMENTS

The present invention relates to a method of separating a fluid component from a biologic sample using microsphere beads. The present invention further relates to a device and a method for analyzing the presence or absence of an analyte in a biologic fluid sample. The invention also relates to quantifying with precision the amount of one ore more analytes present in a biologic fluid sample. The present invention further relates to an assay which can interpret test results and be used to further identify certain medical conditions from which a person or animal may be suffering or is likely to suffer from in the future. The present invention further relates to a prognostic assay technique in which the results of the test assay defined in the present invention may be used to predict the likelihood of a person or animal developing a certain condition or disease state at a future time. These various embodiments are described in detail herein.

Although the preferred embodiments described herein are described with respect to the testing of human biologic samples it is well understood that such assays and methodologies could equally be used for assessing biologic samples in other animals. In particular the present invention would clearly have applicability to veterinary services.

In a biologic fluid sample having a fluid component and a non-fluid component, the fluid component containing an analyte of interest the present invention may be used to measure any of the following, alone or in combination:

a) the presence of the analyte in the sample
b) the absence of the analyte in the sample
c) concentration of the analyte in the sample
d) total amount of analyte in the sample.

Suitable analytes which may be measured by the assay and device of the present invention include soluble analytes: including but not limited to, enzymes, proteins, bacteria, viruses, antigens, antibodies, immunoglobulins, drugs, and hormones. Other suitable analytes would be known to one skilled in the art. The assay and device of the present invention are useful for the detection and measurement of drugs of abuse in human biologic samples such as performance enhancing drugs or other street drugs.

Some biologic samples can be assayed without first separating out cellular components; however, for example, in the case of blood, the cellular component can interfere with the assay. In the case of biologic samples where it is necessary, or preferred, to remove the cellular component before assaying it is necessary to first separate the fluid component from any cellular components. In the case of blood, for example, it is necessary to separate the plasma from the whole blood so that the cellular components of the blood do not interfere with the testing for the analyte which is present in the plasma.

It is recognized in the present invention, surprisingly, the fluid component of a biologic sample can be separated from its non-fluid component by applying the sample to a grouping of microsphere beads. When the sample is applied the fluid component will flow in between microsphere beads thereby separating it from the cellular components in a simple and effective way. The beads act as a means of separating the fluid component from the non-fluid component as the fluid component moves by capillary action, through the spaces formed between the beads, when the beads are grouped together. So, in the case of blood, the plasma is separated from the cells in the blood sample. It has been surprisingly recognized in the present invention that microspheres have the ability to separate out the plasma from whole blood quickly and efficiently.

For the purposes of this patent application the spaces between the beads are called "interstitial spaces" or "pores". It is believed that the fluid flows by capillary action from one interstitial space to the next.

In the present application the flow of the fluid passing through the interstitial spaces between the beads is likened to flowing along channels formed by the spaces between the beads. The channels are referred to as "capillary" channels because it appears that the fluid flows between the beads by "capillary" action.

When the microspheres are grouped together small spaces, interstitial spaces, are formed between the microsphere beads. The size of the space formed between the microspheres is a function of the radius of curvature of the microspheres. The radius of curvature is, for the purposes of the present invention, the same as the diameter of the microsphere. To understand the relationship between the microsphere bead size and the pore size which is formed between the beads, it is known that the ratio of the microsphere diameter to pore diameter is approximately 1 to 0.4. In the case of separating out the plasma from whole blood, a pore size of 4 Tm is considered optimal. Therefore, the bead size for this particular embodiment should be 10 Tm. This permits an easy fluid flow (and therefore faster fluid flow) while still preventing cells from passing through the pores. The small spaces formed between the beads provide a certain capillarity when a fluid is present.

In the present invention the use of microspheres is an effective and inexpensive means for separating plasma from whole blood as the erythrocytes and leukocytes in the blood will stay on one side of the beads while the plasma portion of the blood sample will pass through the beads, by capillary-like action along the interstitial spaces or pores, formed between the beads. It is considered that the capillary action observed in the present invention is related to the surface tension exerted by the microspheres on the fluid so as to draw the fluid forward. As the fluid is drawn forward between the microspheres it provides the additional advantage of mobilizing any reagents present in the region of the microspheres. For example, the microsphere layer could be impregnated with secondary antibodies or another detection molecule.

The microsphere beads are effectively acting as a fluid filter and as such can be used at any point in an assay where simple fluid filtration is required. Since it is believed that the microspheres act to filter the fluid component from the non-fluid component by capillary action, the microsphere filter may be termed a capillary filter and this term is used for that purpose herein.

The microspheres could have analyte specific antibodies bound to them, for example, by adsorption or coupling. As the fluid containing the plasma passes through the capillary channels formed by the microspheres the analyte will mobilize the secondary antibodies contained on the microspheres and then react with the primary antibodies contained in the biochip. However, the microspheres may act solely to separate the cellular component from the fluid component and the microspheres need not be labeled with antibodies.

Prior art technology has used chromatographic paper or other fibrous material to wick the fluid component of a biologic sample away from the cellular component in order to perform tests on the fluid portion without interference from the cells or other substances present in the sample. The microspheres of the present invention provide an advantage over the prior art technology because it provides improved fluid flow without restriction by the fiber which is present in the chromatographic paper. The microspheres provide a further advantage in that they provide an excellent surface for binding of proteins such as antibodies or other suitable labels.

The size of the microsphere beads used to separate the fluid component can be varied based on the viscosity of the sample. Larger beads should be used for more viscous samples for faster fluid flow between the beads. Also, beads of different colours may be used to facilitate visualization of the beads when they are used as labels and bind to the analyte. The bound beads also serve to increase the density of any bound analyte for subsequent detection by a spectrometer. The regular pattern of the beads also means that diffraction difference could be used for detecting and measuring bound analyte.

The biologic sample may be applied to the top of the beads or at the side of the beads.

In a preferred embodiment latex microsphere beads are used such as those available from Bang's Laboratories, Inc. (Fishers, Ind., USA). The beads are supplied in a liquid suspension. The beads can either be kept moist or dried when used. Other types of beads could be used in the invention, including glass, so long as the beads separate out the fluid component from the non-fluid component.

The use of microsphere beads to quickly separate out a fluid component from a biologic sample can be incorporated into assays for detecting and quantifying analytes present in the sample.

According to one aspect of the present invention this method of separating out a fluid sample from a biologic sample using microsphere beads is incorporated into a one-step assay for analyzing one or more analytes which may be present in the fluid sample is provided. The assay is performed in association with a chamber of defined volume. In a preferred embodiment the chamber comprises microsphere beads for separating out the fluid sample and detection means for detecting and/or measuring an analyte in the sample. The detection means may be drawn from any of several known methods for detecting an analyte in a sample. For example the analyte may be recognized using detection protein, such as an antibody or antigen, which is specific to the analyte. When the analyte binds to the detection protein it changes density and may be measured. Alternatively, the detection protein may be bound to another label, which can be detected. For example the detection protein may be attached to a small bead so that when the detection molecule binds to the analyte the density will increase and this can be detected or measured. Other suitable labels would include metals such as gold, fluorescent labels, chemical labels, or colorimetric labels.

In accordance with an aspect of the present invention, this invention pertains to a point-of-care diagnostic or prognostic test in the form of a small chip or cassette for use in assaying biologic samples such as blood. The present invention teaches a small, compact assay device referred to as a "biochip" for a simple assay taught in accordance with the present invention.

In the device of the present invention there is a pairing together of two carrier surfaces in order to define a specific volume in which a quantitative measurement of analyte(s) present in a drop of blood, urine, saliva or other biologic fluid may be measured. In a preferred embodiment the surfaces in question are a coverslip and a microscope slide but the present invention is not intended to be limited to only these specific embodiments. An important aspect of the present invention is the fact that a fluid sample enters a space of defined volume by capillary action. The defined space is therefore referred to herein as a capillary chamber. In the case of a microscope slide and coverslip the capillary chamber is that volume of space between the bottom of the cover slip and the top of the slide.

In accordance with a preferred embodiment of the present invention, the amount of fluid which is present between the plates or slides is determined by the volume of space between the slides. Therefore small test systems can be designed which allow for precision testing of very small volumes, in some cases, as small as a few microliters.

In order to quantitatively measure the concentration of an analyte in a sample and to compare test results from one test to another it is advantageous to have a consistent test volume of the fluid sample each time the assay is performed. In this way the analyte measurement is assessed directly without having to adjust for varying volumes. The concentration or quantity of analyte can be assessed directly without difficulty and with consistency from test to test. The chamber of the biochip of the present invention provides that defined volume.

In accordance with one aspect of the present invention the fluid volume in which the measurement of an analyte is performed is standardized. In accordance with another aspect of the present invention a method is provided for separating the plasma from the blood cells in a very small blood volume since it is most practical to be able to perform these tests with only a droplet of blood, for example from a finger prick, rather than requiring a larger volume only available by taking a tube of blood through a needle.

In one preferred embodiment the biochip test devices comprises a chamber of a determinable volume. The chamber is defined by first and second opposed carrier surfaces. The surfaces are positioned so that they are separated by a distance which is sufficiently narrow to permit fluid to flow between the two surfaces by capillary action. The chamber has a defined volume as it forms a defined space. The chamber has one or more points of fluid entrance which allow a fluid sample to enter. In this application, the chamber is also referred to as a capillary chamber since the fluid enters by capillary action.

For the purposes of the present invention this arrangement of the two carrier surfaces joined together is referred to as a "biochip" but may also be known as a cassette or cartridge.

The intention is to provide a compact, portable test system which may be standardized. In a particularly preferred embodiment the bottom surface is, for example, a microscope slide and the top surface is a microscope coverslip. Microscope slides and coverslips are readily available and therefore are useful carrier surfaces. In another example two microscope slides could be mounted one on top of the other, or any two plates, so long as there is a defined space between the plates of a determinable volume into which a fluid sample flows by capillary action.

Once in the capillary chamber, the fluid sample is retained by way of surface tension at the ends and edges of the two surfaces. The device is of a small size which makes it portable and it can be inserted into an analyzer and reaction products between the analyte and detection molecules are measured using the analyzer. For the purposes of describing certain preferred embodiment the carrier surfaces will be referred to as plates; however, the invention is not to be limited only to flat plates. Similarly, all types of surfaces which are able to bind proteins, antigens and other detection molecules are contemplated with the scope of the present invention. Specifically the composition of the carrier surface includes, but is not limited to, glass, plastic and metal.

In a preferred embodiment of the present invention a drop of biologic sample is placed on the top surface of the microscope slide and, before entering the capillary chamber, the cellular component of the sample is removed by movement of the fluid component through a grouping of microsphere beads. For example, in the case of blood, the plasma is separated from the cellular component of blood by movement through capillary channels formed by interstitial spaces between the beads and then the fluid enters the testing chamber in which the analyte reacts with reagents in the chamber and the reaction product is a measure of the analyte present in the sample.

Once the fluid has entered the defined space it is exposed to one or more reagents present on an interior face of a carrier surface. The reagents are therefore exposed in the capillary chamber and available for reacting with one or more analytes which may be present in the fluid sample which ultimately fills the capillary chamber. The reagents are labelled and the quantity of analyte present in a fluid sample is measured based on a reaction product which results from the interaction of the analyte in the sample with the reagent in the chamber. The test results are then compared to standard calibrations to determine the quantity of analyte present in the sample. In a preferred embodiment of the present invention the reagent is one or more analyte specific antibodies which are adhered to the carrier surface, preferably by protein printing.

Alternatively, in another embodiment, an antigen is present on an interior face of the carrier surface and the amount of antigen specific antibody in the sample is measured. When bound to the carrier surface the protein or other detection molecule will project into the defined space where it can react with the analyte in the sample. The detection molecule which is present on the interior face of the carrier surface may be bound to the surface by any one of several means known to a person skilled in the art.

Detection molecules are either coated, printed or otherwise bound to one plate or the other using one of several techniques well known in the art. Numerous techniques for immunoassays are known to persons in the art and are described, for example, in "Principles and Practise of Immunology" (1997), C. P. Price and D. J. Newman eds. (Stockton Press) and this document is hereby incorporated by reference into the instant patent application and made a part hereof as if set out in full herein.

The distance between the two plates is limited only by the ability of the plates to effectively draw a fluid such as plasma between the two plates by capillary action and to retain the fluid in the defined volume. The size of the plates used would also be dictated by practical considerations such as the desired volume for testing. Plates of larger surface areas would yield higher volumes.

In accordance with the present invention a fluid sample such as a drop of blood is placed at one edge of the two plates and is drawn into the space defined between the plates. A fluid sample could be drawn against the edge of the two plates by any number of means which would be known to a person skilled in the art. In its simplest form the sample could be brought directly to touch the edges such that a portion of the fluid sample is drawn into the space so as to completely fill the defined volume of the space. For example by touching the patient's finger to the plate. It is important in the present assay that the sample always fill the defined volume entirely so that suitable quantitative analysis may be performed. In a standardized model the volume would be consistent from one biochip to another.

In another preferred embodiment the plates are joined together such that the fluid sample may be readily removed. For example, at the end opposite the point of fluid entry.

In another example, the space between the two plates could be divided into lanes and the volume of each lane would similarly be known. This approach would allow multiple tests to be done on a single sample.

When dealing with a blood sample in which one wishes to measure a plasma protein it is necessary to separate the plasma from the cells. In the present invention it is desirable that the test results be made available in a short time frame, preferably on the order of 1 to 30 minutes, from beginning to end. An advantage of the present invention is that the fluid sample enters the test chamber in a shorter time than prior art assays since the use of microsphere beads to separate the plasma from the blood sample, for example, eliminates the delay which would occur using fiberglass or chromatographic strips. Cumbersome equipment such as a centrifuge is not required for cell separation. All of which facilitates the test being performed at the point-of-care.

The present invention has further advantages over the prior art since the biochip device of the present invention permits several assays to be performed on one sample. This facilitates the speed with which test results can be obtained and minimizes the amount of sample required for testing.

Analyte-specific antibodies themselves may be labeled with anyone of several labels known to persons skilled in the art of such assays. Examples of preferred labels include fluorescent labels, colorimetric labels, another microsphere, gold particles or any high contrast molecule. Other labels would be suitable so long as the presence of the label can be detected. Similarly microsphere beads having a diameter which is smaller than the test beads can be used so that the smaller beads are mobilized through the larger beads with the movement of the fluid sample (e.g. plasma). The smaller beads can be labeled accordingly.

When the fluid sample containing the analyte enters into the defined space between the two plates a further antibody-antigen reaction may occur. In the present invention the upper plate, for example a coverslip, has analyte-specific reagents bound on the surface which comes in contact with the fluid. In a preferred embodiment of the present invention the analyte-specific reagents are printed on the interior surface of the carrier plate using a protein printer. Suitable protein printing devices are well known in the marketplace. These include ink jet, spray, piezo-electric and bubble jet protein printers. The piezo-electric printer is preferred. The analyte-specific reagent acts as a detection molecule, typically proteins. These molecules adhere to glass, metal and plastic surfaces. Preferred surfaces include polystyrene or polypropylene. The use of such printing devices is advantageous in the present invention to allow several different analyte-specific detection molecules to be printed onto the plate or coverslip such that different "lanes" are defined and different analytes may be assessed simultaneously using a single fluid sample. Additional background and calibration lanes can be provided in the same test chamber.

Figure 1:
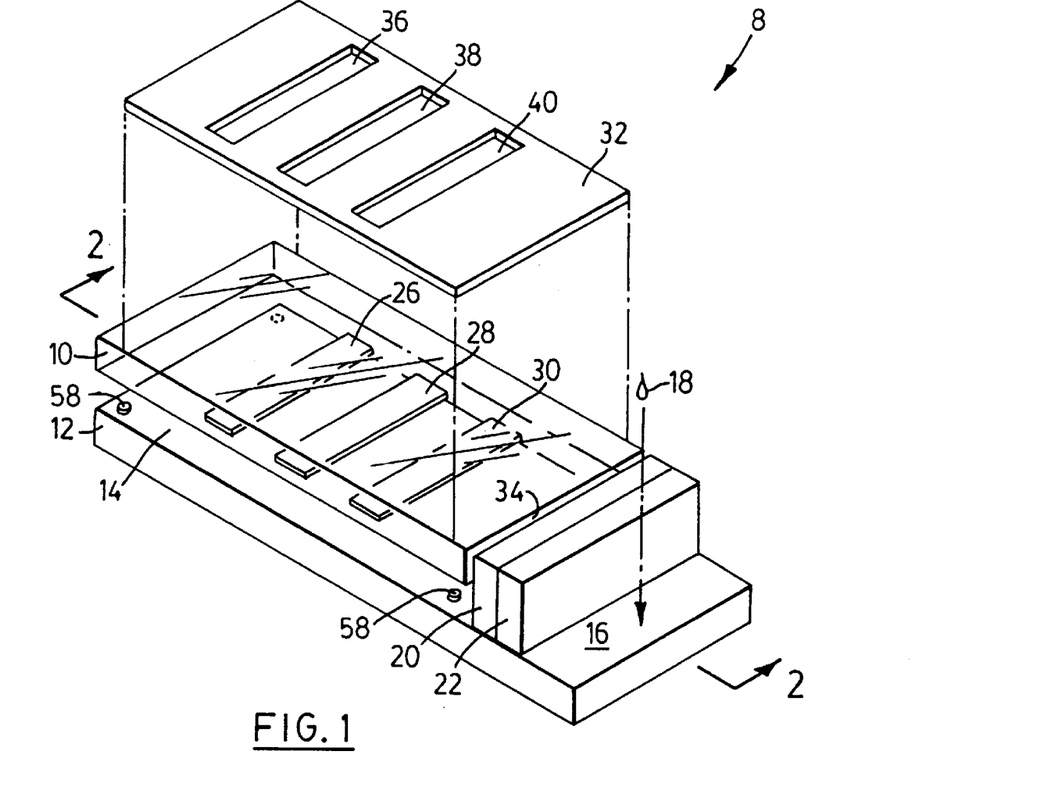
FIG. 1 is an schematic, exploded, perspective view of an embodiment of the device of the present invention.

After the analyte reacts with the analyte-specific detection molecule a measurable reaction product will be produced. It is preferred that the biochip carrier surfaces be colorless or transparent such that a colorimetric, or fluorescent or other reaction products can be read using a suitable spectrometer or other appropriate detection coupled to a reader. When the analyte and analyte-specific detection molecule react together there is a change in density in the reaction lane. In a preferred embodiment of the present invention, the change in density is measured to determine the amount of analyte present in the sample. In order to reduce the background noise and therefore increase the sensitivity of the assay a mask is provided in accordance with a preferred embodiment of the present invention. Referring to FIG. 1 the mask 32 is made of an opaque material except for the openings 36, 38 and 40 which correspond to lanes 26, 28 and 30 on the plate. The mask is designed to fit neatly over the upper plate 10 so that only the lanes themselves are available to be read. The use of the mask has the advantage of reducing the amount of background noise and setting baseline values when reading the density change in the lanes.

In a prefer aspect of the present invention, the biochip is designed to be read by a portable spectrometer which reads for example, the change in color after the analyte has reacted with the labeled antibody. The spectrometer could also read changes in density, film thickness, mass absorption or diffraction depending on the test reagents used. Once the analyzer, e.g. spectrometer, has performed the necessary data calculations the results are transmissible by digital transmission over the telephone lines or other computer network system. Alternatively, changes occurring during an antibody/analyte reaction may be detected or measured by changes in radio frequency if a radio frequency sensor is incorporated into the biochip detection system.

Turning to the figures, FIG. 1, a preferred embodiment of the biochip of the present application is illustrated in a schematic exploded perspective view. Two carrier plates 10 and 12 are provided. The two plates define a fixed volume therebetween as indicated by reference number 14. Lower plate 12 may be longer than upper plate 10 to provide a shelf which acts as an application zone 16 upon which a biologic sample 18 may be applied. A shelf is not essential to the invention but provides a place to allow the sample to be separated by the microsphere beads. It is possible that the beads could be placed at the entrance of the capillary chamber 14 within the confines of the plates and the sample would be applied to the edge of the biochip where it would enter the chamber by capillary action.

Also affixed to application zone 16 is a collection of microsphere beads 20 which may or may not also include a label zone 22. The microsphere beads 20 may be grouped or bundled using a fluid-permeable material. For purposes of the schematic illustration, in FIGS. 1 and 2, the microsphere beads 20 and label zone 22 are illustrated as separately defined regions; however the microsphere beads may also bear the label themselves and in this embodiment the two zones would converge into one with the microsphere beads playing two roles: separation of the fluid and displaying a label to which the fluid is exposed.

More than one size of microsphere beads may be present. In one embodiment, smaller microspheres could nestle in the interstitial spaces formed by the larger beads. The smaller beads could carry secondary labels which would bind to the analyte as it passes through the beads. Either the label would bind to the analyte in the fluid or the label attached to the small bead would attach to the analyte in the fluid and the small beads would then travel with the fluid into the capillary chamber. At the same time any cellular component in the fluid sample would not pass through the microsphere bead filter.

A patient ID may be affixed to either plate 10 or 12 so long as it does not interfere with the test detection areas on the biochip or with reading the biochip after analyte has reacted with the substance bound to the carrier plate surface. The plates 10 and 12 are preferably colorless and/or transparent.

Three detection areas 26, 28, 30 are printed on the inner surface of carrier plate 10: a calibration print zone 26, a detector print zone 28 and a baseline print zone 30. Three detection areas, or zones, are depicted for example only to illustrate how one test biochip may be set up; however, several lanes may be present and the number of lanes dedicated to calibration and/or background can vary depending on what is being tested.

The test need not be limited to only three lanes. Several lanes could be defined. In a preferred embodiment of the present invention three lanes are printed on the one plate to permit assessment of background readings as well as calibration of the biochip. It is understood that the background and calibration detection zones need not all be placed on the same biochip. It is advantageous to have the background and calibration readings made on the sample carrier plate in the same assay as the test analyte thereby reducing the variance in test results.

A background mask 32 is optionally provided. The mask is designed to cover the outer surface of the carrier plate 10 without blocking the coated or printed detection zones/lanes. Therefore, openings 36, 38 and 40 are, for example, present in the mark to reduce background interference when reading test results. The background mask is made of an opaque material with openings 36, 38 and 40 which correspond to the detection zones 26, 28 and 30 identified on the inner surface of the upper plate. The opening 40 in the mask need not have a corresponding test zone 30 as illustrated so long as the opening 40 is exposed to a part the plate 10 where reagents are not present.

Figure 5:
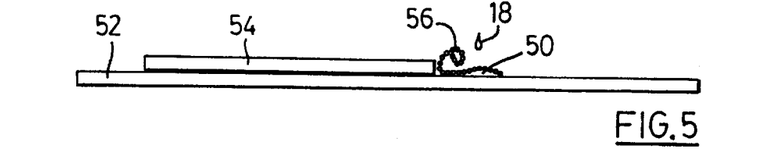
FIG. 5 is another side view of an embodiment described in Example 1 illustrating the position of the cover slip in relationship to the beads on the microscope slide.
Figure 6:
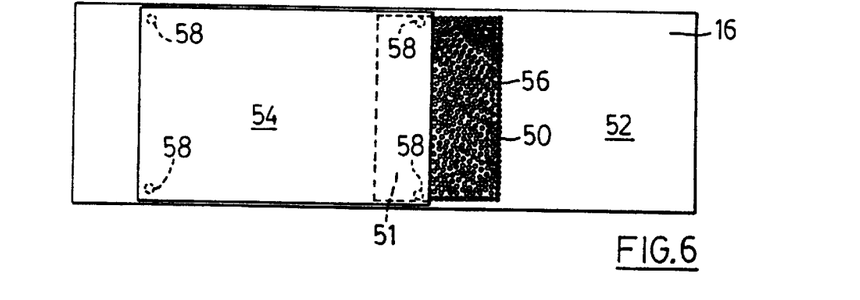
FIG. 6 is a top plan view of an embodiment described in Example 1.

Although FIG. 1 illustrates both an antibody/label zone 22 and a microsphere zone 20, both of these zones are optional depending on the type of test one chooses to conduct. When fluid sample 18 is applied to application zone 16 it flows through antibody/label zone 22 (if present) and microsphere bead zone 20 (if present) before it reaches the edge 34 where the two plates 10 and 12 first meet. In the schematic illustration of FIG. 1 there is a gap between the zone of microsphere beads and the fluid entry point identified by edge 34. Although this arrangement of the invention will work, it would be most preferred if the microsphere bead zone 20 and/or label zone abutted against the edge 34 of the carrier plate 10. One example of such a configuration is illustrated in FIGS. 5 and 6. This configuration provides the least distance for the fluid sample to travel and this further minimizes the amount of fluid sample required for testing and is described in greater detail in Example 1.

The fluid sample is drawn under edge 34 into the chamber 14 which defines a known volume. The fluid sample should be of sufficient volume to pass along the application zone 16, through the microsphere and label zone(s) and to completely fill the chamber 14. The biochip of the present invention can be scaled to a small size such that a single drop of blood could be a sufficient sample size for testing. Many dimensions are possible to construct based on the principles taught herein. Although dimensions of 1 cm×3 cm make a device of convenient size, the nature of the testing to be done would dictate the optimum chip size. As illustrated in FIG. 1 a shelf portion 16 extends on the bottom plate. On this shelf portion the biologic sample can be applied. In other embodiments, the portion of the test which is held, for example the microscope slide, may be large but the test assay itself which sits on the slide may be very small. The assay may be miniaturized to accommodate sample fluid volumes as small as about 1 microlitre.

Figure 2:
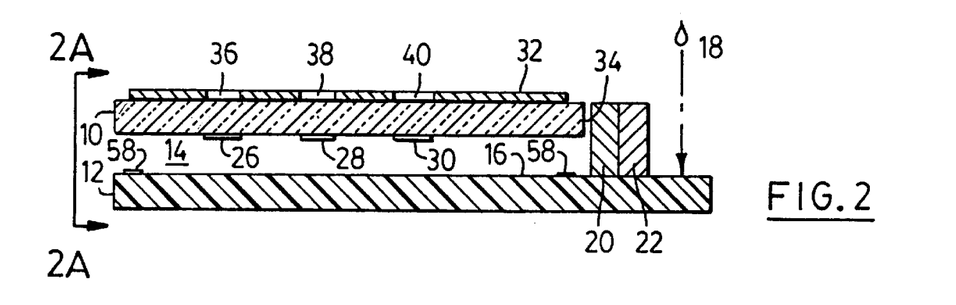
FIG. 2 is a longitudinal cross section of the preferred embodiment illustrated in FIG. 1 along line 1A—1A.
Figure 2A:
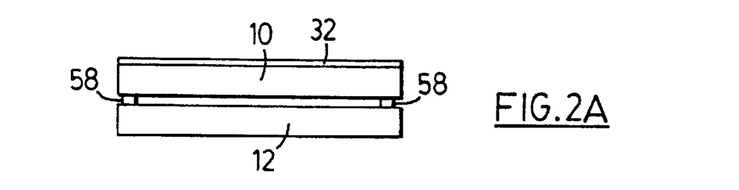
FIG. 2A is an end elevation view of the device illustrated in FIG. 2 taken from the perspective of line 2A—2A.
Figure 3:
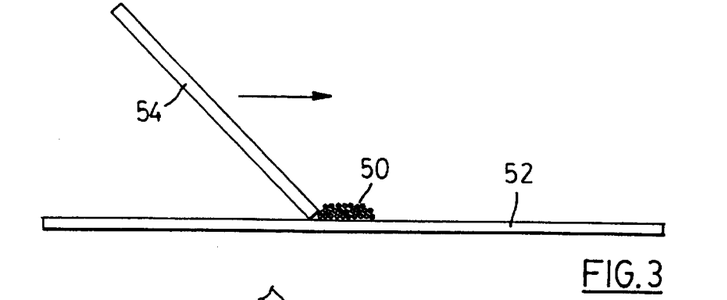
FIG. 3 is a side view of an embodiment described in Example 1 illustrating the cover slip in relation to the beads when starting to form the curl.
Figure 4:
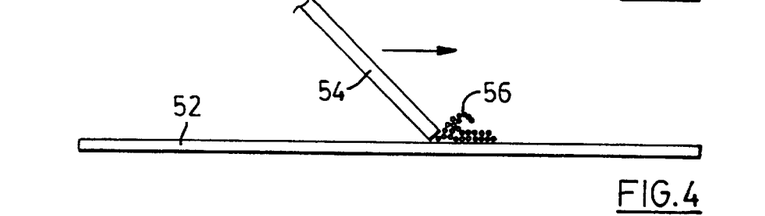
FIG. 4 is also a side view of an embodiment described in Example 1 illustrating the curl after formation.

FIG. 2 is a sectional view taken along lines 2—2 illustrating the same elements as referenced in FIG. 1. FIG. 2A is an end elevation view of FIG. 2 along lines 2A—2A illustrating that the end of the device may be open, to allow the fluid to be removed from the chamber. One would want to remove fluid from the chamber, for example, is you wanted to test the whole sample. A suitable wicking material would be applied to the open end and the fluid would be drawn through thereby allowing additional fluid to enter the chamber. This could be either a continuous or a discontinuous process.

Illustrated in all of FIGS. 1, 2 and 2A is a spot of glue 58 which is one way to hold the plates 10 and 12 together. The glue 58 also illustrated in FIG. 6, another embodiment of the invention.

Figure 7:
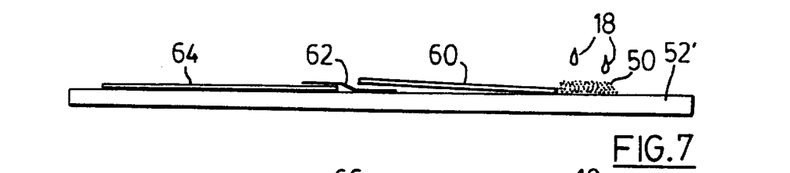
FIG. 7 is a side view of an embodiment described in Example 2 illustrating the label pad variant.
Figure 7A:
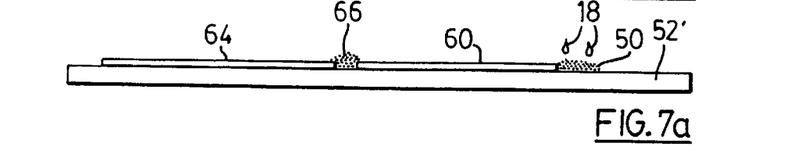
FIG. 7A is a side view of another embodiment described in Example 2 illustrating the replacement of the label pad with microsphere beads.

FIGS. 7 and 7A are illustrations of another use of the microsphere method of separation in a one-step assay. In this embodiment the microspheres are used in conjunction with chromatography paper. The biologic sample 18 is placed on a surface such as a microscope slide 52'. It may be placed directly on the microsphere beads 50 (as illustrated) or beside them. The fluid component of the sample then flows through the beads 50 separating from a non-fluid component present in the sample 18. The beads abut against or sit close to a fiberglass filter pad 60 which abuts with a label pad 62. The label pad 62 is usually a fiberglass pad impregnated with the label of interest for labeling analyte in the fluid sample. The fluid flows through the filter 60 and label pad 62. Any analyte present in the fluid will be labeled as it flows through the label pad. The fluid then flows into the nitrocellulose chromatography strip 64 where the test results are read, usually as a color change or band on the nitrocellulose strip. Alternatively, since the microspheres 50 are used as a filter, the fiberglass filter 62 may be eliminated entirely (not illustrated).

Finally, as illustrated in FIG. 7A, the fiberglass label pad 62 may be replaced by microsphere beads 66. In this case the beads 66 are acting as a source of label, not as a filter and the fiberglass filter 60' serves as a spacer between the two sets of beads 50 and 66, respectively. For applications where filtration of a fluid component is not required, the microspheres 66 can be used to label an analyte present in the fluid directly, without requiring the microsphere filter 50 or the fiberglass spacer 60'.

FIGS. 7 and 7A are illustrative of how current assay methodologies may be modified using the microsphere bead technology of the present invention as taught herein.

The assay device and techniques of the present invention are very useful in that they can be used for small volumes of many kinds of fluid samples. Although the description refers specifically to proteins any number of other marker would be suitable so long as a labeling system can be devised for the detection and measurement of the marker in the system. For example, the present invention could be used to measure and/or detect the presence of microorganisms such as bacteria, viruses, fungi or other infectious organisms. The biochip device of the present invention can be calibrated for the type of assay and the type of analyte so that a table of standard values may be constructed. The assay system or the present invention can detect the levels of a particular hormone or even the amount of a drug in a patient's system and this standardized data can be used to make diagnostic and/or prognostic determinations for a given individual.

Figure 8:
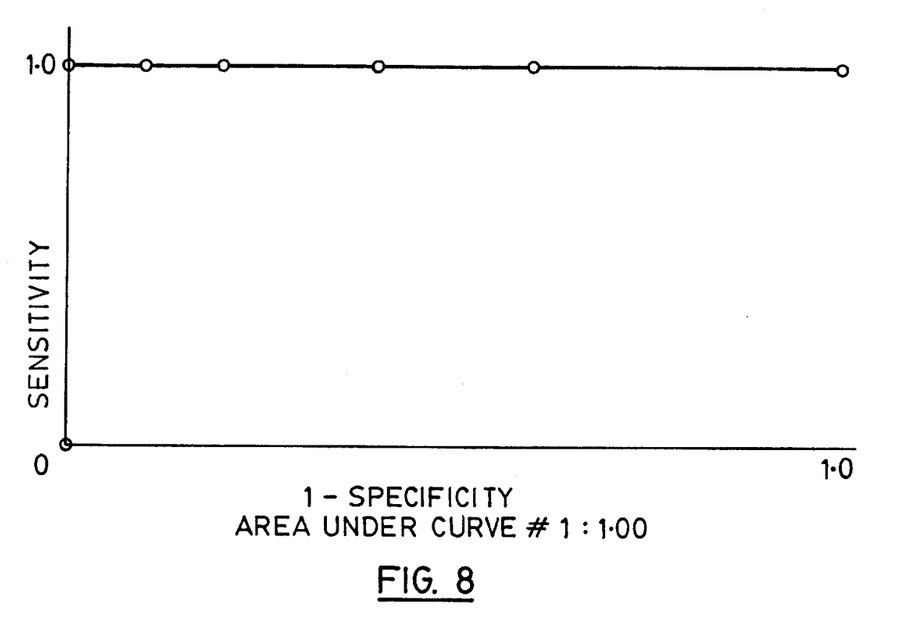
FIG. 8 illustrates an example ROC curve for the expected test results for a neural network risk analysis test.

Once the table of standard values is constructed data is collected on a regular basis and databases constructed based on the patient's medical history, current health and the test results. Optionally, the data can be transmitted by digital transmission systems over a computer network via modem, the internet, cable lines, telephone lines, satellite or other similar technology. These databases can be used in the development of neural network algorithms, for assessment of current patient test results and diagnoses as well as for predicting certain health outcomes for a given individual. One example of a neural network algorithm is found in Example 3 below and a sample Receiver Operator Curve (ROC) is illustrated in FIG. 8.

The development of the algorithms for the applied neural network will be a function of the medical condition being assessed. Large amounts of patient data will first have to be accumulated in order to have reliable predictive outcomes. The neural network can be trained to recognize the concentration of analyte which is diagnostic or prognostic, using the standardized assays of the present invention. The data and algorithms are encoded in an electronic chip which is placed in the reader, for example a spectrometer, such that the printout from the reader will also identify a particular diagnosis or prognosis simultaneously with providing the test result. In the neural network algorithms, the diagnostic or prognostic test result will be optimized as the number of data points increases. With more patient data the predictive and/or diagnostic result will be made with greater certainty. The percent certainty can be calculated and provided to the physician or technician based on analysis of the measured data in comparison to a database contained in an electronic memory chip installed in the analyzer provided. Present technology makes it possible to display the actual standard curve on the reader itself at the time of printing out the test results.

In addition to the use of a spectrophotometer, and in accordance with another aspect of the invention, the biochip has a radiofrequency sensor incorporated into the carrier plate 10. When a reaction takes place in one or more detection areas a measurable change in radio frequency occurs and by detecting this change in radio frequency the presence or the absence or even the extent of a reaction can be measured or detected using a suitable device for detecting radio frequency changes.

In the present invention, more than one test can be run simultaneously on the same biochip and therefore the certainty of the diagnosis or prognosis can be improved. As the number of markers increases so does the certainty of measurement.

One of the many examples of uses of the biochip/cassette of the present invention is to measure blood proteins indicating peripheral vascular disease using a drop of the patient's blood.

Further details of the preferred embodiments of the invention are illustrated in the following Examples which are understood to be non-limiting with respect to the appended claims.

EXAMPLE 1

Verification of Plasma Flow and Separation from Whole Human Blood

As illustrated schematically in FIGS. 3 to 6, approximately 15 microliters of 10 micrometer latex microsphere beads 50 (Bang's Laboratories, Inc., Fishers, Ind., USA) were dropped onto a glass slide 52 and allowed to dry. A glass coverslip 54 was placed on the slide and pushed, on edge, towards and along, the dried beads. The cover slip caused the dried beads to be separated from the glass slide and further caused the collection of dried beads to roll over thereby forming a curl 56. The cover slip was then placed on the slide with the "curl" touching the edge of the coverslip (illustrated in FIGS. 5 and 6). The coverslip was fixed squarely in place on the slide with one edge aligned parallel to the edge of the curl of dried beads and this edge was left open to allow fluid to pass through the beads and into the capillary chamber formed between the cover slip and the glass slide. The coverslip was attached with nail polish at the corners 58 of the coverslip to secure it to the microscope slide. The coverslip was secured at a spot where no capillary action was intended to take place to permit fluid to flow freely under the coverslip.

A 20 microliter drop of whole human blood 18 was placed on the remaining 5 to 10 microliter microsphere beads. In other words, the sample of whole human blood was placed on the remaining portion of the beads which did not form part of the curl leaving the plasma component free to move by capillary action through the curl portion of the microsphere beads and into the space defined between the coverslip and the slide (i.e. the capillary chamber). The effect was observed under a binocular light microscope. Upon application of the blood sample to the beads the plasma immediately began to separate from the whole blood. As the curl became plasma soaked, capillary action between the coverslip and the slide drew the pure, clean, cell-free plasma under the coverslip into the chamber defined between the coverslip and the slide. This chamber defines a known space, the volume of which can be calculated and predetermined.

This demonstrated that the microsphere beads are able to readily and effectively separate plasma from whole blood and to pass, via the capillary channels formed between the microsphere beads, into the capillary chamber.

EXAMPLE 2

Microsphere Separation Combined With Chromatography Strip

In an assay for an analyte in a human blood sample, this example (schematically illustrated in FIG. 7) demonstrated the use of microsphere separation of plasma from a blood sample of human whole blood. The plasma was separated using latex microsphere beads (Bang's™) 50 and then drawn into a standard nitrocellulose chromatography strip.

The fiberglass pads, which are usually used to retain red blood cells in the prior art, were replaced with about 20 microliters of 10 micrometer latex beads. A drop of human blood (about 60 microliters) was placed on a surface 52', in contact with the latex microspheres. The fiberglass pad 60 effectively functions as a spacer between the beads 50 and the label pad 64 although it could also be used as a second filter. The fiberglass filter 60 may be eliminated entirely and the microsphere beads 50 abut directly with the label pad 64 (not illustrated).

It was observed that the blood soaked the bead pile and within about 2 minutes clear plasma ran onto the nitrocellulose chromatography strip. This was observed with the visible eye and also under a microscope. This example demonstrated that the microsphere method for separation of plasma from blood can also be used in conjunction with a standard nitrocellulose chromatography strip. For tests using such chromatography strips this is clearly an advantageous methodology for separating plasma from blood.

Illustrated in FIG. 7A is another embodiment where, instead of a fiberglass label pad 62, microsphere beads 66 are used as the label region of the test device. The fiberglass filter pad 60' is used as a spacer between the two sets of beads, 50 and 66.

EXAMPLE 3
Neural Network Marker Analysis

A neural network is a mathematical function $N(W,a)$ which takes input analyte vectors $a=(a1, a2 \ldots, an)$ and outputs numbers between 0 and 1. The weight parameters W are adjusted during the training period, using training patterns $\{p=(b1,b2,\ldots bn, T)\}$ where $b1, \ldots, bn$ are training protein vectors, and T is the target output value. In the case of a coagulation test, T would be 1 for coagulation, and 0 for a non-coagulation.

The parameters W are adjusted to minimize the error $$E = \sum_p (N(W, a) - T)^2$$

while maintaining good performance on new test data.

Once the Network is trained, a network cutoff C is chosen to classify test data. Let $TST(C,b,T)$ be the test result for a testing vector a, given cutoff C, and target output T.

$$TST(C, b, T) = \begin{cases} 1 & \text{if } N(a) > C \\ 0 & \text{otherwise} \end{cases}$$

Now, we can analyze the sensitivity and specificity of the test.
True Positive if $T=1$ and $TST(C,b,T)=1$
False Positive if $T=0$ and $TST(C,b,T)=1$
True Negative if $T=0$ and $TST(C,b,T)=0$
False Negative if $T=1$ and $TST(C,b,T)=0$
Sensitivity=TP/(TP+FN)
Specificity=TN/(TN+FP)

Plotting sensitivity versus 1-specificity for various cutoffs gives a ROC (receiver operator characteristic) curve.
Neural Networks We start with a set of training patterns $\{p=(I1, I2 \ldots I1, TAR\}$, where Ij is an input value and TAR is the target value (TAR=0 or TAR=1). We want to train a neural network to give outputs which are close to the target values.

A neural network has 3 layers; the first INPUT layer, the second HIDDEN layer, and the third OUTPUT layer:

The neurons are connected by a set of weights $\{w(i,j,k)\}$. For example, $w(1,2,4)$ connects the second neuron of the first layer with the fourth neuron of the second layer.

For each pattern we assign a number called the activation to each neuron, which measures the probability that it is firing. The activation is defined recursively as follows:

$$a(i,j) = \begin{cases} Ij & \text{if } i=1 \\ 1/(1+exp(-sum(k)\{w(i-1,k,j)a(i-1,k)\})) \end{cases}$$

The error is calculated as $$ERMS = SQRT\{sum\{(t-a(2,1))^2\}\}$$

where the sum is over all patterns.

The weights are adjusted to minimize ERMS, while maintaining good performance on new data.

Those skilled in the art will recognize, or be able to ascertain using no more than routine experimentation, many equivalents to the embodiments of the invention described specifically above. Such equivalents are intended to be encompassed in the scope of the following claims.

I claim:

1. A device for separating fluid from a biologic sample, the sample having a fluid component and a non-fluid component, the device comprising:
   a flat base having first and second portions, said first portion being adjacent to said second portion; and a plurality of microspheres, said microspheres being located on said first portion and in fluid communication with said second portion, said microspheres further being disposed in abutting relation and forming interstitial spaces therebetween such that the interstitial spaces connect to form a plurality of capillary channels, whereby when the microspheres are disposed in fluid communication with the biologic sample, the non-fluid component is separated from the fluid component by capillary flow of the fluid component through the capillary channels onto said second portion;

said plurality of microspheres comprising a plurality of smaller microspheres interspersed among a plurality of larger microspheres, the plurality of larger microspheres being disposed in substantially abutting relation and forming interstitial spaces therebetween such that the interstitial spaces connect to form a plurality of capillary channels, the plurality of smaller microspheres being sufficiently small in size such that they occupy the interstitial spaces formed by the larger microspheres and move through the capillary channels and are carried forward by the fluid component as it, flows through the capillary channels.

2. The device of claim 1 wherein the smaller microspheres are labeled with at least one label.

3. The device of claim 2 wherein the label is selected from the group consisting of radioactive labels, fluorescent labels, metals, proteins, peptides, antigens and antibodies.

4. The device of claim 2 wherein the biological fluid contains an analyte and the label is an antibody having a specificity directed to the analyte.

5. The device of claim 1 wherein the plurality of smaller microspheres further comprises a plurality of groups of microspheres, each group being impregnated with a different label and each group being interspersed among the larger microspheres in a separate zone of the larger microspheres.

6. A device for separating fluid from a biologic sample, the sample having a fluid component and a non-fluid component, the device comprising:
a plurality of larger microspheres, said larger microspheres being disposed in abutting relation and forming interstitial spaces therebetween such that the interstitial spaces connect to form a plurality of capillary channels, whereby when the larger microspheres are disposed in fluid communication with the biologic sample, the non-fluid component is separated from the fluid component by capillary flow of the fluid component through the capillary channels; and
a plurality of smaller microspheres, the smaller microspheres being interspersed among the plurality of larger microspheres and being sufficiently small in size such that the smaller microspheres occupy the interstitial spaces formed by the larger microspheres and move through the capillary channels and be carried forward by the fluid component as the fluid component flows through the capillary channels.

7. The device of claim 6 wherein the smaller microspheres are labeled with at least one label.

8. The device of claim 7 wherein the label is selected from the group consisting of radioactive labels, fluorescent labels, metals, proteins, peptides, antigens and antibodies.

9. The device of claim 7 wherein the biologic fluid contains an analyte and the label is an antibody specific for said analyte.

10. The device of claim 6 wherein the plurality of smaller microspheres further comprises a plurality of groups of microspheres, each group of microspheres containing a different label and each group of microspheres being interspersed among the larger microspheres in a different zone of the larger microspheres.

11. The device of claim 6 wherein sizes of the microspheres ate selected according to a viscosity of the sample.

12. The device of claim 6 wherein the microspheres are bundled in a fluid-permeable material.

13. The device of claim 6 wherein the microspheres are maintained in abutting relation by a surface tension of the fluid or by drying the microspheres.

14. The device of claim 6 further comprising fluid-conveying means for conveying the sample into fluid communication with the microspheres.

15. The device of claim 6 wherein the biologic sample is blood and the fluid component is plasma.

16. A device for separating fluid from a biologic sample, the sample having a fluid component and a non-fluid component, the device comprising;
a flat base having first and second portions, said first portion being adjacent to said second portion; and
a plurality of microspheres located on said first portion and in fluid communication with said second portion, said microspheres further being disposed in abutting relation and forming interstitial spaces therebetween such that the interstitial spaces connect to form a plurality of capillary channels;
wherein the size of the microsphere is selected according to a viscosity of the sample and whereby when the microspheres are disposed in fluid communication with the biologic sample, the non-fluid component is separated from the fluid component by capillary flow of the fluid component through the capillary channels onto said second portion;
said plurality of microspheres comprising a plurality of smaller microspheres interspersed among a plurality of larger microspheres, the plurality of larger microspheres being disposed in a substantially abutting relation forming interstitial spaces therebetween such that the interstitial spaces connect to form a plurality of capillary channels, the plurality of smaller microspheres being sufficiently small in size such that the smaller microspheres occupy the interstitial spaces formed by the larger microspheres and move through the capillary channels and be carried forward by the fluid component as the fluid component flows through the capillary channels.

17. The device of claim 16 wherein the smaller microspheres are labeled with at least one label.

18. The device of claim 17 wherein the label is selected from the group consisting of radioactive labels, fluorescent labels, metals, proteins, peptides, antigens and antibodies.

19. The device of claim 17 wherein the biologic fluid contains an analyte and the label is an antibody specific for said analyte.

20. The device of claim 16 wherein the plurality of smaller microspheres further comprises a plurality of groups of microspheres, each group of microspheres containing a different label and each group of microspheres being interspersed among the larger microspheres in a different zone of the larger microspheres.

21. A device for separating fluid from a biologic sample, the sample having a fluid component and a non-fluid component, the device comprising:
a flat base having fit and second portions, said first portion being adjacent to said second portion; and
a plurality of microspheres located on said first portion and in fluid communication with said second portion, said microspheres further being disposed in abutting relation and forming interstitial spaces therebetween such that the interstitial spaces connect to form a plurality of capillary channels, the microspheres being bundled in a fluid-permeable material;

whereby when the microspheres are disposed in fluid communication with the biologic sample, the non-fluid component is separated from the fluid component by capillary flow of the fluid component through the capillary channels onto said second portion;

said plurality of microspheres comprising a plurality of smaller microspheres interspersed among a plurality of larger microspheres, the plurality of larger microspheres being disposed in a substantially abutting relation forming interstitial spaces therebetween such that the interstitial spaces connect to form a plurality of capillary channels, the plurality of smaller microspheres being sufficiently small in size such that the smaller microspheres occupy the interstitial spaces formed by the larger microspheres and move through the capillary channels and be carried forward by the fluid component as the fluid component flows through the capillary channels.

22. The device of claim 21 wherein the smaller microspheres are labeled with at least one label.

23. The device of claim 22 wherein the label is selected from the group consisting of radioactive labels, metals, proteins, peptides, antigens and antibodies.

24. The device of claim 22 wherein the biologic fluid contains an analyte and the label is an antibody specific for said analyte.

25. The device of claim 22 wherein the plurality of smaller microspheres further comprises a plurality of groups of microspheres, each group of microspheres containing a different label and each group of microspheres being interspersed among the larger microspheres in a different zone of the larger microspheres.

* * * * *